(12) United States Patent
Massow et al.

(10) Patent No.: US 9,243,889 B2
(45) Date of Patent: *Jan. 26, 2016

(54) DEVICE FOR OPTICAL COHERENCE TOMOGRAPHY

(71) Applicant: Wavelight Gmbh, Erlangen (DE)

(72) Inventors: Ole Massow, Nuremberg (DE); Henning Wisweh, Süpplingenburg (DE)

(73) Assignee: Wavelight GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/567,995

(22) Filed: Dec. 11, 2014

(65) Prior Publication Data

US 2015/0092197 A1    Apr. 2, 2015

Related U.S. Application Data

(63) Continuation of application No. 13/789,947, filed on Mar. 8, 2013, now Pat. No. 8,941,840.

(30) Foreign Application Priority Data

Mar. 8, 2012    (DE) .................... 20 2012 002 375 U

(51) Int. Cl.
  *G01B 11/02*    (2006.01)
  *G01B 9/02*    (2006.01)
  *A61B 3/10*    (2006.01)
  *G01N 21/47*    (2006.01)

(52) U.S. Cl.
  CPC ............ *G01B 9/02091* (2013.01); *A61B 3/102* (2013.01); *G01B 9/02072* (2013.01); *G01B 9/02084* (2013.01); *G01N 21/4795* (2013.01)

(58) Field of Classification Search
  USPC .......................... 356/497, 451, 521, 504, 479
  See application file for complete search history.

(56) References Cited

U.S. PATENT DOCUMENTS

| | | | |
|---|---|---|---|
| 8,941,840 B2 * | 1/2015 | Massow ................ | A61B 3/102 356/496 |
| 2009/0196477 A1 | 8/2009 | Cense et al. | |
| 2011/0109911 A1 | 5/2011 | Podoleanu .................... | 356/451 |

OTHER PUBLICATIONS

Hillman, T. R. et al, "The effect of water dispersion and absorption on axial resolution in ultrahigh-resolution optical coherence tomography", Optics Express, Mar. 21, 2005, vol. 13[6], pp. 1860-1874.

Marks, D. L. et al, "Autofocus algorithm for dispersion correction in optical coherence tomography", Applied Optics, Jun. 1, 2003, vol. 42[16], pp. 3038-3046.

(Continued)

*Primary Examiner* — Tri T Ton

(57) ABSTRACT

In certain embodiments, a device for optical coherence tomography (OCT) includes a signal detection device and a computer arrangement. The signal detection device is designed to detect an interference signal ($G(\omega)$) for an object to be imaged in an optical frequency range ($\omega$). The computer arrangement is designed to determine intermediate signals ($G1(k)$, $G2(k)$) in a spatial frequency range (k) from the intermediate interference signal ($G(\omega)$), whereby each of the intermediate signals ($G1(k)$, $G2(k)$) is dispersion-compensated for a different depth (z1, z2) of the object. A locally resolved image signal (FFT1, FFT2) is determined for each of the intermediate signals ($G1(k)$, $G2(k)$) by applying a Fourier transformation to the particular intermediate signal ($G1(k)$, $G2(k)$). A tomography signal ($G(z)$) is determined from the image signals (FFT1, FFT2).

6 Claims, 2 Drawing Sheets

(56) References Cited

OTHER PUBLICATIONS

Figure 1:
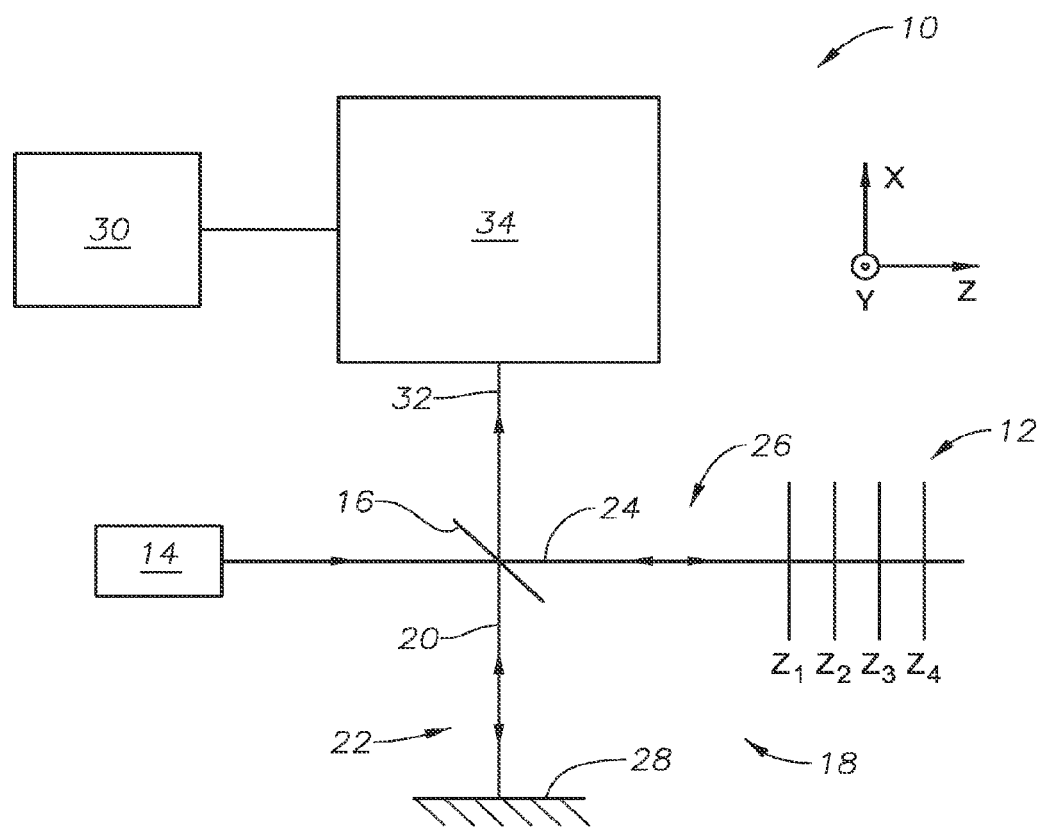

Marks, D. L. et al, "Digital algorithm for dispersion correction in optical coherence tomography for homogeneous and stratified media", Applied Optics, Jan. 10, 2003, vol. 42[2], pp. 204-217.

Sekhar, S. C. et al, "A New Technique for High-Resolution Frequency Domain Optical Coherence Tomography", ICASSP 2007, International Conference on Acoustics, Speech and Signal Processing, 2007, S. pp. 425-428.

Tumlinson, A. R., et al, "Inherent homogenous media dispersion compensation in frequency domain optical coherence tomography by accurate k-sampling", Applied Optics, Feb. 10, 2008, vol. 47[5], pp. 687-693.

Wojtkowski, M., et al, "Ultrahigh-resolution, high-speed, Fourier domain optical coherence tomography and methods for dispersion compensation", Optics Express, May 31, 2004, vol. 12[11], pp. 2404-2422.

Drexler, W., et al, "Optical Coherence Tomography—Technology and Applications", Springer-Verlag, Berlin Heidelberg New York, 2008.

* cited by examiner

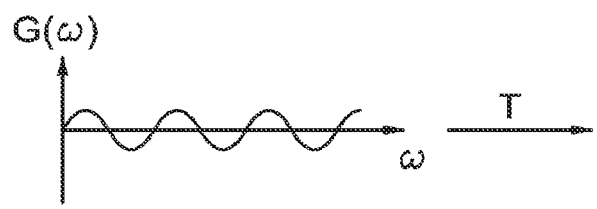
FIG. 2a
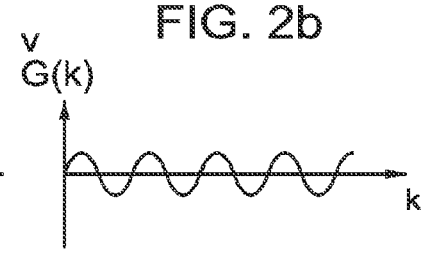
FIG. 2b
FIG. 2c
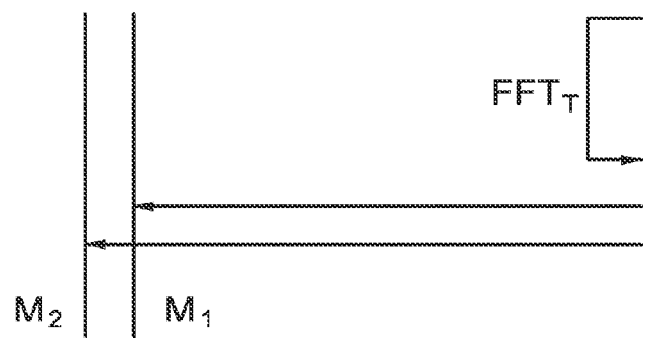
FIG. 2d
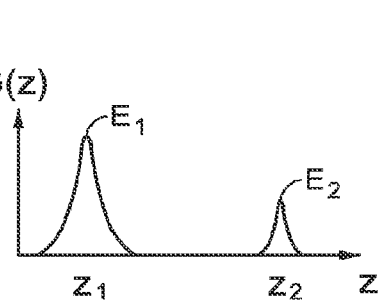
FIG. 2f
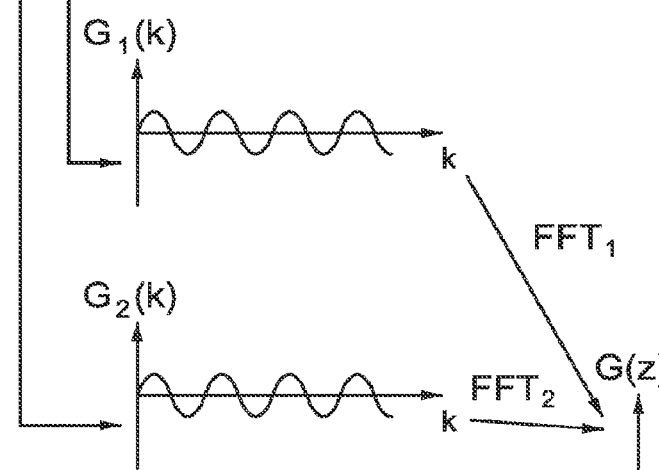
FIG. 2e
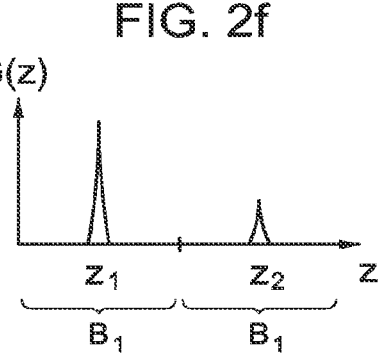

DEVICE FOR OPTICAL COHERENCE TOMOGRAPHY

CROSS REFERENCE TO RELATED APPLICATIONS

The present application is a continuation of U.S. application Ser. No. 13/789,947, filed Mar. 8, 2013, titled "DEVICE FOR OPTICAL COHERENCE TOMOGRAPHY," (now allowed), which claims priority under 35 USC 119 of German Utility Model Application No. 202012002375.6, filed Mar. 8, 2012, titled "DEVICE FOR OPTICAL COHERENCE TOMOGRAPHY," the disclosures of which are incorporated by reference in their entirety.

TECHNICAL FIELD

The invention relates to a device for optical coherence tomography.

BACKGROUND

Optical coherence tomography OCT serves to provide a one-, two- or three-dimensional (1D, 2D or 3D) tomogram of an object to be investigated. A coherent light beam with a defined coherence length is directed along an object arm onto the object. The object reflects or scatters the light of the light beam into different measuring depths. A reflection or scatter occurs especially on optical boundary surfaces of the object, on which the refraction index of the object changes. The light scattered back from the object is then superposed by a coherent light beam from a reference arm for obtaining an interference signal. The positions of the depth of the boundary surfaces are coded in the phase information and/or in the modulation frequency of the interference signal.

Due to a wavelength-dependent refraction index inside the object, dispersion can occur that can result in a loss of the axial resolution with increasing measuring depth. Resolution loss inside of the tomograms can blur the representation of boundary surfaces and structures of the object, whereby the latter may appear, for example, widened or smeared in the tomogram. Consequently, for example, closely adjacent boundary surfaces cannot be separated from each other with sufficient accuracy.

In order to obtain tomograms with a high resolution, the dispersion should be compensated for by, for example, purely optical measures. This can also be applicable in an adapted manner to large dispersions in high-resolution systems for certain sections or boundary surfaces.

In order to obtain dispersion-compensated raw data, equivalent optical path lengths are generated along the object arm and the reference arm, for example, by introducing identical media in the object arm and the reference arm. The dispersion can be compensated for only for a single, previously defined depth, therefore, for the passage through a fixed optical wavelength. On the other hand, dispersion compensation adapted for several depths can be generated by several optical compensations adapted to the particular depths. This requires a plurality of separate and expensive measurements with a changed optical compensation each time of the optical wavelength and/or of the dispersion for the particular depth. In addition, as a result of the plurality of separate measurements, the inherent accuracy of the position of boundary surfaces that would result from only one OCT measurement is lost.

Further information about dispersion compensation in OCT systems can be obtained from the publications listed in Appendix A attached hereto.

SUMMARY

One task of the present invention is to indicate a device for optical coherence tomography that makes possible a determination of tomograms of an object to be investigated with high resolution.

This task may be solved by a device with the features of claim 1. It makes possible a section-by-section numeric dispersion compensation.

DETAILED DESCRIPTION OF EXAMPLE EMBODIMENTS

The present invention is based on the following recognition: A spatial widening of a measuring signal, where widening is a function of the measuring depth and based on a dispersion caused by the object medium, cannot be differentiated per se from a measuring signal error that is a function of the measuring depth and that is caused during the obtention of a tomography signal by an incorrect association instruction during the conversion of an optical frequency into a spatial frequency.

This means on the other hand: If the dispersion caused by the object medium up to a certain measuring depth is known, dispersion compensation can be carried out by association instructions adapted to the measuring depth. Accordingly, different association instruction s are required for different measuring depths. Accordingly, a corresponding number of association instruction s must also be provided for a number of measuring depths to be investigated for which the tomography signal should finally be present as an image of the object with a high axial resolution.

A device for the optical coherence tomography comprises a signal detection device designed to detect an interference signal for an object to be imaged in an optical frequency range. Furthermore, the device comprises a computer arrangement designed to determine a plurality of intermediate signals in a spatial frequency range from the interference signal, whereby each of the intermediate signals is dispersion-compensated for a different depth of the object. The computer arrangement is furthermore designed to determine a locally resolved image signal for each of the intermediate signals by applying a Fourier transformation on the particular intermediate signal and to determine a tomography signal from the image signals.

In other words: since the depth positions of the boundary surfaces inside the object are coded in the phase information and/or modulation frequency of the interference signal (raw data) and the dispersion inside the object medium has an influence on the phase information of the interference signal, the interference signal must be subjected to a phase correction for the dispersion compensation, whereby the phase correction is adapted for its part to the depth of the particular boundary surface. Accordingly, the dispersion can be compensated for layers of the object, which are separated from each other by the boundary layers, with different refraction indices by applying a layer-by-layer phase correction. The layer-by-layer application is based here on the determining of a plurality of intermediate signals from the interference signal that are dispersion-compensated for the different depths of the object. Subsequently, a Fourier transformation can be carried out for each of the dispersion-compensated intermediate signals. Thus, a multiple application of adapted Fourier transformations takes place that supply a locally resolved image of the object for each of the intermediate signals. The individual images are subsequently combined to a total image.

Therefore, embodiments of the present invention makes it possible to detect boundary surfaces and structures at different depths of the object and the distances of boundary surfaces and structures of the object with a high or the highest possible resolution by a dispersion compensation adapted to certain depths or depth ranges. "Highest possible resolution" denotes here the axial resolution of the tomogram that theoretically results from the coherence length of the light used for the OCT.

The optical coherence tomography can be, for example, the FD (English: Fourier domain) OCT or a sub-variety of it, for example, SD (English: spectral domain) OCT or SS (English: swept source) OCT. The object can be samples that can be detected, measured and/or imaged with OCT. In particular, the object has several boundary surfaces. The object is, for example, a human eye.

The interference signal is produced from the interference of a coherent light beam scattered back from the object to be imaged or investigated inside an object arm with a coherent light beam scattered back from a reference object inside a reference arm. The interference signal can represent intensity or an intensity distribution. The interference signal can be detected in a known manner in the framework of optical coherence tomography and can be understood as the raw data signal.

The optical frequency range can be represented, for example, by the frequency f or the angular frequency $\omega$ (with $\omega = 2\pi f$). The interference signal then represents, for example, a function or distribution $I(f)$ or $I(\omega)$ dependent on the optical frequency f or $\omega$. Accordingly, the interference signal can be understood as a spectrum or a spectral distribution in the optical frequency range. However, the interference signal can also be understood as a standardized spectrum or a standardized spectral distribution in the optical frequency range that is standardized in particular as regards the spectrum emitted by the light source used for the OCT. In this case, the interference signal represents, for example, a function or standardized distribution $G(f)$ or $G(\omega)$ dependent on the optical frequency f or $\omega$.

An intermediate signal can represent intensity, a standardized intensity, an intensity distribution or a standardized intensity distribution.

The spatial frequency range can be represented, for example, by the wave number k (with $k = 2\pi n/\lambda$ with n as refraction index and $\lambda$ as wavelength). The wave number k is to be understood as a spatial frequency. An intermediate signal can represent, for example, a function or distribution $I(k)$ dependent on the wave number k. Accordingly, an intermediate signal can be understood as a spectrum or a spectral distribution in the optical frequency range. However, an intermediate signal can also be understood as a standardized spectrum or a standardized spectral distribution in the optical frequency range. In this case, the intermediate signal represents, for example, a standardized function or standardized distribution $G(k)$ dependent on the wave number k.

The computer arrangement can be designed to determine each of the intermediate signals starting from the interference signal using association instructions (such as pre-sampling or mapping). "Determine" can denote a numeric or analytical manipulation of the interference signal. The association instructions can associate a certain spatial frequency k with each optical frequency f or $\omega$. In this case one would speak of a transformation $\omega \rightarrow k$. However, the association instructions can also associate, for example, a spectral distribution $I(k)$ or $G(k)$ in the spatial frequency area with a spectral distribution $I(f)$, $I(\omega)$, $G(f)$ or $G(\omega)$ in the optical frequency range. In this case one would speak of a transformation $(f) \rightarrow I(k)$, $I(\omega) \rightarrow I(k)$, $G(f) \rightarrow G(k)$ and $G(\omega) \rightarrow G(k)$. The association can be a calculation if, for example, the interference signal is present as an analytic function. However, the association can be a point-wise or element-wise allocation if, for example, the interference signal is present in discrete data points. For example, the association instructions can be implemented as a compensation curve or characteristic compensation curve.

"Depth" denotes a measuring depth inside the object or on the object or a measuring depth range, a layer or a segment of the object, in particular a measuring depth range, a layer or a segment of the object with a homogeneous refraction index. Depth can also be understood as the position of a boundary surface or the range around a boundary surface inside the object and/or on the object. A boundary surface can be a surface that separates two areas of the object with different refraction indices from one another and/or that reflects or scatters back a measuring beam serving for the OCT. A boundary surface can denote an optical boundary surface, a boundary layer and/or an optical boundary layer. Measuring depth can also denote the penetration depth to which a measuring beam serving for the OCT penetrates into the object to be investigated until the measuring beam is scattered back or reflected back from the object.

During the determination of the intermediate signals from the interference signal each of the intermediate signals is dispersion-compensated for a different depth of the object. This can take place in that the association instructions selected by the computer arrangement is adapted for the particular depth to the dispersion caused by the object. The selection of the association instructions by the computer arrangement takes place in such a manner that the dispersion that was caused during the passage of the measuring beam for the object medium, which measuring beam had penetrated to the particular (measuring) depth, is taken into account and compensated. By taking account of a characteristic compensation curve (mapping) during the transformation/conversion of the optical frequency info the spatial frequency, the dispersion through the object medium can be eliminated for the particular refraction index dependent on the measuring depth at a certain depth or a certain depth section (for example, given by the spatial resolution capacity of the OCT device). In other words, the same effect can be achieved by an adapted, non-linear resampling of the spectral components of the interference signal for obtaining the intermediate signals. Instead of a single value of the refraction index the latter can also be understood as a (for example, wavelength-dependent and/or locally dependent) refractive index course.

Association instructions can accordingly be implemented as a resampling compensation curve or a mapping curve in the computer arrangement by means of which a scanning of the interference signal for obtaining the intermediate signal takes place in such a manner that the intermediate signal has a period duration that is constant over the spatial frequency. The association instructions can represent the particular non-constant and non-linear course of the dispersion caused by the object medium down to the measuring depth, whereby the course indicates how the optical frequency depends on the spatial frequency spatially/locally.

Since the tomography signal should finally be an image of the object that has the (theoretically) highest possible axial resolution at different measuring depths, the association instructions preferably correspond to the number of the different measuring depths. The Fourier transformation is preferably a fast Fourier transformation (FFT), with which a locally resolved image signal can be rapidly gained from an intermediate signal in a low computer-intensive manner and therefore especially rapidly.

The image signals are finally combined by the computer arrangement to a tomography signal. The computer arrangement can be designed to process the information contained in the image signals in such a manner that the tomography signal is arranged in different areas of the measuring depth. An individual area can be composed exclusively of information of an individual image signal. In particular, an area is determined in such a manner that the measuring depth at which the image signal has the highest possible axial resolution on account of the dispersion compensation is arranged centrally, in the middle in the particular area, whereby the areas can in particular border on each other.

The computer arrangement can be designed to calculate in advance corresponding association instructions for each step, and to file it in a memory, for example, in the form of a look-up table. Alternatively, it is conceivable that the computer arrangement is designed to calculate in advance association instructions for each depth by a model of the object.

Additionally or alternatively, the computer arrangement can be designed to calculate association instructions for the particular depths using an algorithm for the subsequent phase correction of the interference signal. The algorithm is implemented, for example, in the form of a so-called autofocusing, during which the phase correction necessary for the dispersion compensation is automatically calculated.

The (measuring) depth itself as well as the refraction index dependent on the measuring depth and the axial refraction index course dependent on the measuring depth of the object medium, that is passed through down to the (measuring) depth by the measuring beam, can be determined in the framework of the determining of association instructions that should compensate a dispersion caused by the object medium, that was traversed by the measuring beam down to the (measuring) depth.

The depths or depth ranges can be determined by peak detection in the depth determination signal. To this end the computer arrangement can be designed to at first determine an intermediate signal of depth determination in a spatial frequency range from the interference signal using given association instructions for depth determination (mapping). The intermediate signal for depth determination can represent intensity I or a standardized intensity G. It is then possible by determining a locally resolved image signal of depth determination by applying a Fourier transformation to the intermediate signal of depth determination to obtain the different depths for the intermediate signals on the basis of a defection of extreme points of the image signal of depth determination that represent local changes of the refraction index in the object. The determination of the extreme points can take place with the aid of known image processing methods implemented in the computer arrangement.

The determination of the intermediate signal of depth determination by the computer arrangement can take place by a numeric or analytic manipulation of the interference signal: The association instructions for depth determination can associate a determined spatial frequency k, for example, with every optical frequency f or ω. The association instructions for depth determination can, however, also associate a spectral distribution I(k) or G(k) in the spatial frequency area with a spectral distribution I(f), I(ω), G(f) or G(ω) in the optical frequency range. The association can be a calculation if, for example, the interference signal is present as an analytic function. However, the association can also be a point-wise or element-wise allocation if, for example, the interference signal is present in discrete data points. For example, the association instructions can be implemented as a compensation curve or characteristic compensation curve.

The association instructions for depth determination can be given and filed in a memory of the computer arrangement. The association instructions for depth determination can be adapted to a given dispersion, for example, to a dispersion caused for a determined depth through the object medium. This depth corresponds, for example, to an empirical value located, for example, in the area of boundary surfaces of the object, which area is to be examined. Alternatively, association instructions can also be applied to the interference signal in which instructions no dispersion of the object to be investigated is taken into account.

Furthermore, the computer arrangement can be designed to apply a Fourier transformation, in particular, a rapid Fourier transformation on the intermediate signal for depth determination and to obtain a locally resolved image signal for depth determination. Preferably, one or more extreme point(s), or one or more other point(s) of the image signal for depth determination that represent(s) the depth position(s) of one boundary surface/boundary surfaces is/are determined by the computer arrangement using image processing in the image signal for depth determination.

Additionally or alternatively, even intervals from the imaging signal for depth determination that are related to measuring depths, in particular one or more intervals of (extreme) points of the image signal for depth determination can be determined by the computer arrangement using image processing. It is also conceivable to determine the dispersion produced during the passage through a layer of the object, which dispersion is a function of the optical wavelength traversed, in particular of the layer thickness and the refraction index of this layer. The refraction index of the object medium can be measured, for example, using the device. Alternatively, the refraction index can be determined by the computer arrangement from a model of the object to be investigated in which a plurality of refraction indices is filed for different areas, i.e., layers of the object to be investigated.

The dispersion and then the association instructions required for the compensation of these dispersions can be determined from the previously cited parameters by the computer arrangement. In other words: Association instructions are calculated preferably on the basis of the depth positions and/or the mutual intervals of selected points, in particular the extreme points of the image signal for depth determination taking into account one or more refraction indices that is/are characteristic for the object medium in areas up to the positions of the extreme points.

Alternatively or additionally, the computer arrangement can also be designed to determine association instructions by using a Hilbert transformation.

The invention is explained in detail in the following using the attached drawings, in which FIG. 1 shows in a schematic representation elements of a device for optical coherence tomography in accordance with an exemplary embodiment, and FIG. 2a to 2f show in a schematic representation dispersion compensation carried out by the device in FIG. 1.

The device for optical coherence tomography in FIG. 1—designated in general there by 10—serves to prepare tomograms of an object 12. The object 12 can represent, for example, a human eye.

The device 10 comprises a light source 14 for the emission of coherent light. The light source 14 is designed, for example, as a light source variable in the optical frequency range or is arranged to emit a broadband spectrum of coherent light in the optical frequency range. The light emitted by the light source 14 is directed onto a beam divider 18. The beam divider 16 is a component of an interferometer 18 and divides the incident optical output according to a given dividing ratio, for example, 50:50. The one beam 20 runs inside a reference arm 22 and the other beam 24 (the measuring beam) runs inside a specimen arm or object arm 28. Instead of the 3-space setup shown in FIG. 1 the interferometer 18 can also be realized partially or entirely with the aid of fiber-optic components.

The light of the reference beam 20 branched off into the reference arm 22 strikes a mirror 28 that reflects the light back in a collinear manner on to the beam divider 16. The light of the measuring beam 24 branched off into the specimen arm 26 strikes the object 12 to be investigated, that scatters or reflects the light back in the direction of the beam divider 16. The light of the measuring beam 24 is reflected/scattered back along their propagation direction of the measuring beam 24 at different (measuring) depths $z_1$, $z_2$, $z_3$ and $z_4$. The depths $z_1$-$z_4$ represent in particular boundary surfaces that separate areas/segments of the object 12 with different refraction indices from each other. To this extent the depths $z_1$-$z_4$ can also be understood as the positions of the boundary surfaces up to which the measuring beam 24 penetrated or advanced before it was again reflected or scattered back in a collinear manner.

Other (not shown) optical elements and adjusting components can be provided inside the specimen arm 22 that are designed to focus the measuring beam 24 coming in from the beam divider 18 onto the object 12 and to adjust the focal position (for example, in the lateral directions x, y or in three spatial directions x, y, z, cf. the coordinate system in FIG. 1). A computer arrangement 30 can control the adjusting components for obtaining 1D, 2D and/or 3D tomograms.

The light scattered back from the object 12 in the specimen arm 26 is superposed on the beam divider 16 in a collinear manner with the light reflected by the mirror 28 in the reference arm 22 to an interference beam 32. The optical wavelengths in the reference arm and the specimen arm 22, 26 are substantially equally long so that the interference beam 32 displays an interference between the partial beams 20, 24 from reference arm and specimen arm 22, 26. A detector 34 comprising, for example, one or more photodiodes or designed as a spectrometer detects the intensity G(to) of the interference beam 32, for example, as a function of the angular frequency co. The interference signal $G(\omega)$ represents the raw data signal of the optical coherence tomography and is transmitted to the computer arrangement 30.

The depth positions $z_1$-$z_4$ of the boundary surfaces inside the object 12 are coded in the phase information of the interference signal $G(\omega)$. However, the phase information of the interference signal $G(\omega)$ is also subject in general to an influence by dispersion: While the measuring beam 24 penetrates or advances to the depths $z_1$-$z_4$ the spectral components of the measuring beam 24 collect a phase that is a function of the optical wavelength, i.e., of the wavelength traversed inside the object medium, and of the optical refraction index of the object medium.

Since the refraction index of the object medium is generally a function in a non-constant and non-linear manner of the optical frequency and of the wavelength of the spectral components, dispersion occurs inside the object medium traversed. The dispersion brings it about that the period duration $\Delta\omega$ in the interference signal $G(\omega)$ is short for small angular frequencies co and long for large angular frequencies co, i.e., not constant over co. Finally, the dispersion can lead to a blurred image of the boundary surfaces $z_1$-$z_4$ of the object 12.

As is shown in FIG. 2a to 2f, the computer arrangement 30 carries out a series of method steps starting from the interference signal $G(\omega)$ (see FIG. 2a) for compensating the dispersion (see FIG. 2b to 2e) in order to obtain a tomogram G(z) of the object 12 in which the boundary surfaces are imaged with the (theoretically) highest possible axial resolution along z (see FIG. 2f). This method is explained in detail in the following.

The interference signal $G(\omega)$ can be seen in FIG. 2a, from which the method carried out by the computer arrangement 30 starts. The function $G(\omega)$ describes the intensity of the interference beam 32 in an optical frequency range represented here by the optical angular frequency $\omega$.

At first, a plurality of intermediate signals in a spatial frequency area is determined from the interference signal $G(\omega)$. Two such intermediate signals $G_1k$ and $G_2k$ are shown in FIGS. 2d and 2e. The spatial frequency is represented here by the wave number k.

Each of the intermediate signals $G_1k$ and $G_2k$ is determined starting from the interference signal $G(\omega)$ using association instructions: The intermediate signal $G_1k$ is determined from the interference signal $G(\omega)$ using the association instructions $M_1$ while the intermediate signal $G_2k$ is determined from the interference signal $G(\omega)$ using association instructions $M_2$.

The association instructions $M_1$, $M_2$ assign a distribution $G_1k$ and/or $G_2k$ in the spatial frequency area k to the distribution $G(\omega)$ in the optical frequency range $\omega$, i.e., $M_1$: $G(\omega) \rightarrow G_1k$ and $M_2$: $G(\omega) \rightarrow G_2k$. The particular-association can be a calculation if, for example, the interference signal $G(\omega)$ is present as an analytic function. However, the association can also be a point-wise or element-wise allocation if, for example, the interference signal $G(\omega)$—is present in discrete data points.

The selection of the association instructions $M_1$, $M_2$ takes place in such a manner that each of the intermediate signals $G_1k$, $G_2k$ for a certain depth $z_1$, $z_2$ of the object 12 is dispersion-compensated, whereby $z_1 \neq z_2$. This means that the intermediate signal $G_1k$ represents a distribution $G_1k$ that is dispersion-compensated for the (measuring) depth $z_1$ in the spatial frequency area k and that the intermediate signal $G_2k$ represents a distribution $G_2k$ dispersion-compensated for the (measuring) depth $z_2$ in the spatial frequency area k. In other words: The selection of the association instructions $M_1$, $M_2$ takes place in such a manner that the dispersion that was caused by the object medium traversed by the light beam 24 that advanced to the (measuring) depth $z_1$ or $z_2$ is taken into account and compensated. Association instructions $M_1$, $M_2$ can be understood in this sense as a dispersion compensation.

More precisely stated, the association instructions $M_1$, $M_2$ are implemented as a resampling compensation curve or a mapping curve by means of which a scanning of the curve $G(\omega)$ takes place for obtaining the curve $G_1k$ and $G_2k$ in such a manner that the intermediate signals $G_1k$ and $G_2k$ have different period durations $\Delta k_1$, $\Delta k_2$, that are constant over the spatial frequency k. The association instructions $M_1$, $M_2$ accordingly represent the particular non-constant and non-linear course of the dispersion caused by the object medium down to the measuring depth $z_1$ and $z_2$, as the optical frequency $\omega$ is a function of the spatial frequency k.

Since the tomography signal should finally be an image of the object 12 that has the highest possible resolution along z at different measuring depths $z_1$, $z_2$, the number of association instructions $M_1$, $M_2$ corresponds to the number of different measuring depths $z_1$, $z_2$.

After the determination of the intermediate signals $G_1k$, $G_2k$ a fast Fourier transformation is applied to each of the intermediate signals $G_1k$, $G_2k$, which results for each of the intermediate signals $G_1k$, $G_2k$ in a locally resolved image signal $FFT_1$, $FFT_2$. Accordingly, the image signal $FFT_1$ corresponds to the Fourier-transformed one of $G_1k$ and the image signal $FFT_2$ to the Fourier-transformed one of $G_2k$.

The image signals $FFT_1$, $FFT_2$ are then combined to tomography signal $G(z)$ shown in FIG. 2f. Here, the information contained in the image signals $FFT_1$, $FFT_2$ is processed in such a manner that the tomography signal $G(z)$ is composed in the area Bi exclusively of information of the Fourier-transformed $FFT_1$ of the intermediate signal $G_1k$ and in the area $B_2$ exclusively of information of the Fourier transformed $FFT_2$ of the intermediate signal $G_2k$, whereby the areas $B_1$ and $B_2$ contact one another, for example, at $(z_1+z_2)/2$. In other words: The areas $B_1$, $B_2$ are determined in such a manner that a peak representing the boundary surface at $z_1$ is arranged centrally, that is, in the middle in the area $B_1$ and a peak representing the boundary surface at $z_2$ is arranged centrally in the area $B_2$.

The image sharpness of the tomography signal $G(z)$ gained using the dispersion compensation is reflected in the narrowness of the peak imaged in the tomography signal $G(z)$ at $z_1$, $z_2$, see FIG. 2f. The tomography signal $G(z)$ represents a so-called A-scan, i.e., a one-dimensional tomography of the object 12.

The association instructions $M_1$, $M_2$ are calculated for the particular depths $z_1$, $z_2$ using an algorithm for the subsequent phase correction of the interference signal $G(\omega)$. The algorithm is implemented, for example, in the form of a so-called autofocusing. Here, the phase correction necessary for the dispersion compensation is automatically calculated Since the association instructions $M_1$, $M_2$ should compensate dispersions that were caused by the object medium which was traversed by the light beam 24 up to the (measuring) depth $z_1$ or $z_2$, the depth $z_1$, $z_2$ itself as well as the z-dependent refraction index of the object medium traversed up to the depth $z_1$, $z_2$ are necessary.

The depths $z_1$, $z_2$ are determined, for example, using the method steps shown in FIGS. 2b and 2c that the computer arrangement carries out. At first, an intermediate signal for depth determination $\check{G}(k)$ is determined from the interference signal $G(\omega)$ using association instructions T for depth determination. The intermediate signal $\check{G}(k)$ for depth determination represents an intensity distribution $\check{G}$, see FIG. 2b.

The association instructions T for depth determination allocate a distribution $\check{G}(k)$ in the spatial frequency area k to the distribution $G(\omega)$ in the optical frequency range $\omega$, i.e., T: $G(\omega) \rightarrow \check{G}(k)$. The association can be a calculation if, for example, the interference signal $G(\omega)$ is present as an analytic function. However, the association can also be a point-wise or element-wise allocation if, for example, the interference signal $G(\omega)$ is present in discrete data points.

The association instructions T for depth determination are given and filed in a memory and can be adapted to a given dispersion, for example, to a dispersion caused for a determined depth through the object medium. This depth corresponds, for example, to an empirical value located, for example, in the area to be examined of boundary surfaces $z_1$, $z_2$ of the object 12, preferably in the area of $(z_1+z_2)/2$. Alternatively, association instructions T for depth determination can also be applied to the interference signal $G(\omega)$ at which no dispersion of the object 12 to be examined is considered.

Subsequently, a rapid Fourier transformation $FFT_1$ is applied to the intermediate signal $\check{G}(k)$ for depth determination and a locally resolved image signal $\check{G}(z)$ is obtained, see FIG. 2c. The peaks shown in $G(z)$ have a characteristic peak width that indicates that the A-scan $\check{G}(z)$ shown in FIG. 2c is "blurred".

The extreme points $E_1$, $E_2$ of the image signal $\check{G}(z)$ for depth determination are determined by image processing, which points represent the positions $z_1$, $z_2$ of the boundary surfaces, that is, the z positions of local change of the refraction index in the object 12.

Since the interval of two boundary surfaces furnishes information about how thick the layer of the object medium is, even the intervals $|z_2-z_1|$ of the extreme points $E_1$, $E_2$ are determined in the image signal $\check{G}(z)$ for depth determination. The dispersion produced during the passage through a layer is a function of the optical wavelength traversed, that results from the layer thickness and the refraction index of the object medium of this layer. The refraction index of the object medium can be measured, for example, using the OCT device. Alternatively, the refraction index can be determined from a model of the object 12 to be investigated in which a plurality of refraction indices for different areas, i.e., layers of the object 12 to be investigated are filed.

The dispersions and then the association instructions $M_1$, $M_2$ required for the compensation of these dispersions are now determined from the previously cited parameters. Therefore, it can be said: The association instructions $M_1$, $M_2$ are calculated on the basis of the depth positions $z_1$, $z_2$ and of the mutual intervals $|z_2-z_1|$ of the detected extreme points $E_1$, $E_2$ of the image signal $\check{G}(z)$ for depth determination, taking into account one or more refraction indices that is/are characteristic for the object medium in areas up to the positions $z_1$; $z_2$ of the extreme points $E_1$; $E_2$.

Alternatively or additionally, the association instructions $M_1$, $M_2$ can be determined by applying a Hilbert transformation.

APPENDIX A

Hillman, T. R. & Sampson, D. D., *The effect of water dispersion and absorption on axial resolution in ultrahigh-resolution optical coherence tomography*, Optics Ex-press, 21. März 2005, Vol. 13, No. 6, S. 1860-1874.

Drexler, W. & Fujimoto, J. G., *Optical Coherence Tomography—Technology and Applications*, Springer-Verlag, Berlin Heidelberg New York, 2008.

Tumlinson, A. R., Hofer, B., Winkler, A. M., Povazay, B., Drexler, W. & Barton, J. K., *Inherent homogenous media dispersion compensation in frequency domain optical coherence tomography by accurate k-sampling*, Applied Optics, 10. February 2008, Vol. 47, No. 5, S. 687-693.

Wojtkowski, M., Srinivasan, V. J., Ko, T. H., Fujimoto, J. G., Kowalczyk, A. & Duker, J. S., *Ultrahigh-resolution, high-speed, Fourier domain optical coherence tomography and methods for dispersion compensation*, Optics Express, 31, März 2004, Vol. 12, No. 11, S. 2404-2422.

Marks, D. L., Oldenburg, A. L., Reynolds, J. J. & Boppart, S. A., *Digital algorithm for dispersion mrreciion in optical coherence tomography for homogeneous and stratified media*, Applied Optics, 10. January 2003, Vol. 42, No. 2, S. 204-217.

Marks, D. L., Oldenburg, A. L., Reynolds, J. J. & Boppart, S. A., *Autofocus algo-rithm for dispersion correction in optical coherence tomography*, Applied Optics, 1. Juni 2003, Vol. 42, No. 16, S. 3038-3046.

Sekhar, S. C., Nazkani, H., Blu, T. & Unser, M., *A new technique for high-resolution frequency domain optical*

*coherence tomography*, ICASSP 2007, Inter-national Conference on Acoustics, Speech and Signal Processing, 2007, S. 425-428.

Cense, A. J., Yun, S.-H. & de Boer, J. F., *Process, system and software arrangement for a chromatic dispersion compensation using reflective layers in optical coherence tomography imaging*, US 2009/0196477 A1.

The invention claimed is:

1. A method for optical coherence tomography (OCT), comprising:
    detecting, by a signal detection device, an interference signal ($G(\omega)$) for an object to be imaged in an optical frequency range ($\omega$);
    calculating, by a computer arrangement, for each depth of a plurality of different depths ($z_1$, $z_2$) of the object, association instructions ($M_1$, $M_2$) that correspond to the particular depth ($z_1$, $z_2$) and the dispersion caused by the object;
    determining, by the computer arrangement, a plurality of intermediate signals ($G_1(k)$, $G_2(k)$) in a spatial frequency range (k) from the interference signal ($G(\omega)$) using the corresponding association instructions ($M_1$, $M_2$), each of the intermediate signals ($G_1(k)$, $G_2(k)$) is dispersion-compensated for the different depths ($z_1$, $z_2$) of the object;
    applying by the computer arrangement, a Fourier transformation to each intermediate signal ($G_1(k)$, $G_2(k)$) to determine a locally resolved image signal ($FFT_1$, $FFT_2$) for each of the intermediate signals ($G_1(k)$, $G_2(k)$); and
    determining, by the computer arrangement, a tomography signal ($G(z)$) from the image signals ($FFT_1$, $FFT_2$).

2. The method according to claim 1, further comprising:
    calculating association instructions ($M_1$, $M_2$) with a model of the object.

3. The method according to claims 1 and 2, further comprising:
    determining an intermediate signal ($\check{G}(k)$) for depth determination in a spatial frequency range (k) from the interference signal ($G(\omega)$) using given association instructions (T) for depth determination;
    applying a Fourier transformation ($FFT_T$) to the intermediate signal ($\check{G}(k)$) for depth determination to determine a locally resolved image signal ($\check{G}(z)$); and
    detecting extreme points ($E_1$, $E_2$) of the image signal ($\check{G}(z)$) to determine the different depths ($z_1$, $z_2$) for the intermediate signals ($G_1(k)$, $G_2(k)$).

4. The method according to claim 3, further comprising:
    calculating the association instructions ($M_1$, $M_2$) on the basis of the positions ($z_1$, $z_2$) of the detected extreme points ($E_1$, $E_2$) of the image signal ($\check{G}(z)$) for depth determination.

5. The method according to claim 3, further comprising:
    calculating the association instructions ($M_1$, $M_2$) on the basis of the mutual intervals ($|z_2-z_1|$) of the detected extreme points ($E_1$, $E_2$) of the image signal ($\check{G}(z)$) for depth determination.

6. The method according to claim 3, further comprising:
    calculating the association instructions ($M_1$, $M_2$) using one or more refraction indices that are characteristic for the object medium in areas up to the positions ($z_1$, $z_2$) of the extreme points ($E_1$, $E_2$).

* * * * *